(12) United States Patent
Lee et al.

(10) Patent No.: US 6,988,894 B2
(45) Date of Patent: *Jan. 24, 2006

(54) DENTAL TRAINING DEVICE

(76) Inventors: Charles Q. Lee, 8343 Acuff La., Lenexa, KS (US) 66215; Amy H. Lee, 8343 Acuff La., Lenexa, KS (US) 66215; Wei Tog Dang, 8 Wen Yun Street, Wuyi West Road, Chang Sha, Hunan (CN) 410005

( * ) Notice: Subject to any disclaimer, the term of this patent is extended or adjusted under 35 U.S.C. 154(b) by 0 days.

This patent is subject to a terminal disclaimer.

(21) Appl. No.: 10/767,793

(22) Filed: Jan. 29, 2004

(65) Prior Publication Data
US 2004/0191739 A1 Sep. 30, 2004

Related U.S. Application Data

(63) Continuation-in-part of application No. 10/024,683, filed on Dec. 18, 2001, now abandoned, which is a continuation-in-part of application No. 09/848,739, filed on May 3, 2001, now Pat. No. 6,520,775.

(51) Int. Cl.
*G09B 23/28* (2006.01)

(52) U.S. Cl. ...................... 434/263; 434/262
(58) Field of Classification Search ............... 434/263, 434/264; 433/213
See application file for complete search history.

(56) References Cited

U.S. PATENT DOCUMENTS

| 1,048,382 A | 12/1912 | Allen |
| 1,948,059 A | 2/1934 | Baugh |
| 1,967,786 A | 7/1934 | Schultz |
| 2,005,114 A | 6/1935 | Spitzer et al. |
| 2,256,667 A | 9/1941 | Doret |
| 2,674,802 A | 4/1954 | Williams |
| 3,753,434 A | 8/1973 | Pike et al. |
| 3,886,661 A * | 6/1975 | Neill .................... 434/263 |
| 3,931,679 A | 1/1976 | Carter |
| 3,947,967 A | 4/1976 | Satake |
| 3,950,852 A | 4/1976 | Henning |
| 4,073,071 A | 2/1978 | Angelotti |
| 4,102,047 A | 7/1978 | Walker |
| 4,137,633 A | 2/1979 | Kahn |
| 4,242,812 A * | 1/1981 | Randoll et al. .......... 434/263 |
| 4,846,684 A * | 7/1989 | Oestreich .............. 433/213 |
| 4,969,820 A * | 11/1990 | Oestreich .............. 434/264 |
| 5,108,292 A | 4/1992 | Kirk et al. |
| 5,120,229 A * | 6/1992 | Moore et al. ........... 434/263 |
| 5,211,556 A | 5/1993 | Kobayashi et al. |

(Continued)

FOREIGN PATENT DOCUMENTS

JP 05027675 A * 2/1993

OTHER PUBLICATIONS

*Acadental* brochure on *Bringing the Total Endo Practice to the Classroom*; p. 1-3; Date of Publication 2002.
*Apex Locator Simulation*; Ryan Walker; Date of Publication unknown.

Primary Examiner—Dmitry Suhol
(74) Attorney, Agent, or Firm—John C. McMahon

(57) ABSTRACT

A dental training aid and method which assists a student in learning how to determine the position of a root canal apex, repair of dental decay, and how to perform crown and bridge procedures. In certain embodiments, modular inserts are utilized that include structure thereon for performing root canal procedures, repair of dental decay procedures, crown and bridge procedures or other procedures. The inserts can be assembled and configured to all provide practice on the same procedure or on different procedures and can be exchanged for other inserts once they are no longer reusable or because the user wants to train on a different procedure.

28 Claims, 6 Drawing Sheets

U.S. PATENT DOCUMENTS

| | | | |
|---|---|---|---|
| 5,232,370 A * | 8/1993 | Hoye | 434/263 |
| 5,503,562 A | 4/1996 | Mays | |
| 5,688,118 A * | 11/1997 | Hayka et al. | 433/27 |
| 5,759,159 A | 6/1998 | Masreliez | |
| 6,004,133 A | 12/1999 | Harrison et al. | |
| 6,059,569 A | 5/2000 | Otsuka | |
| 6,520,775 B2 | 2/2003 | Lee | |
| 6,524,105 B2 * | 2/2003 | Raffeiner | 433/213 |
| 6,719,562 B1 * | 4/2004 | Oestreich | 433/213 |
| 2004/0259064 A1 * | 12/2004 | Belvedere | 434/263 |

* cited by examiner

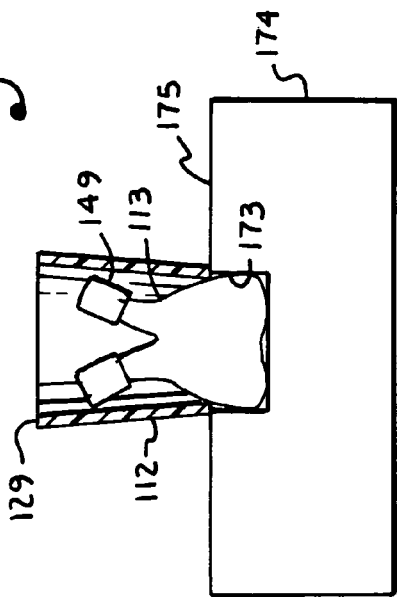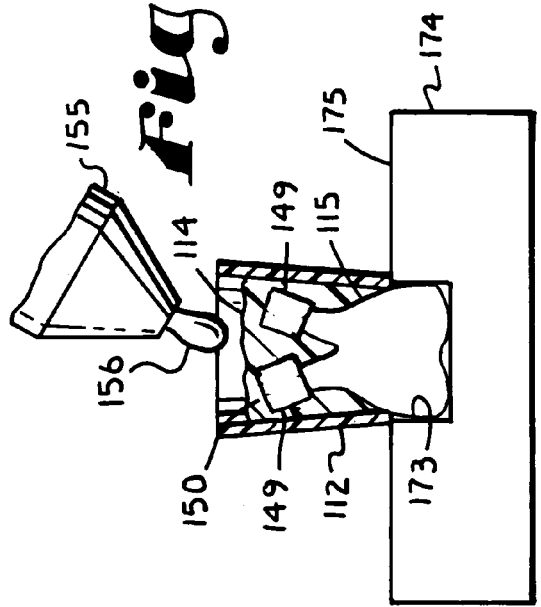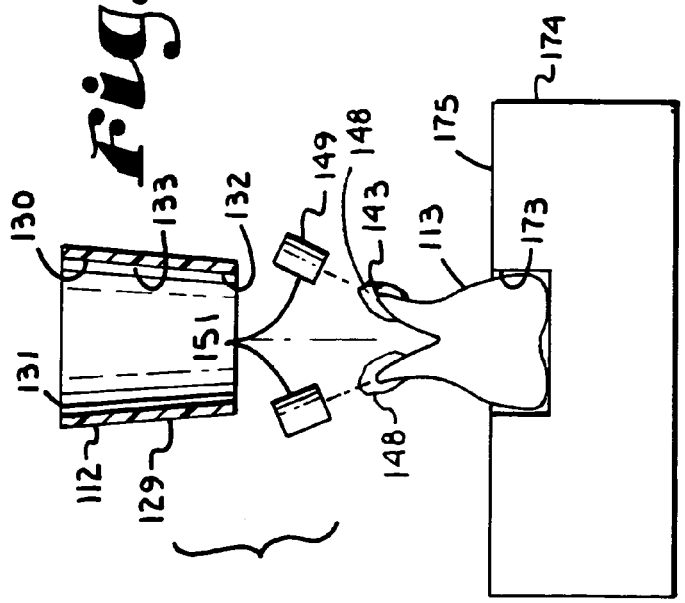

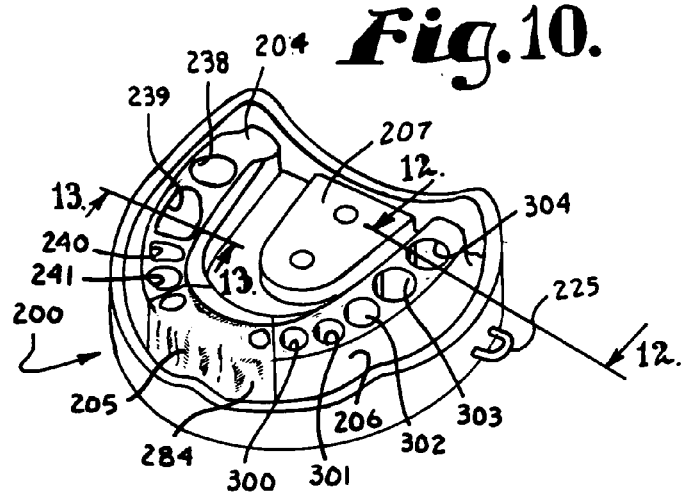
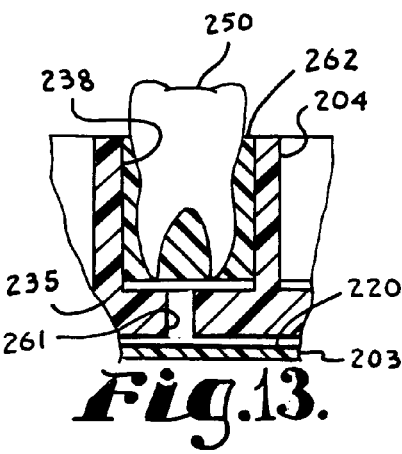
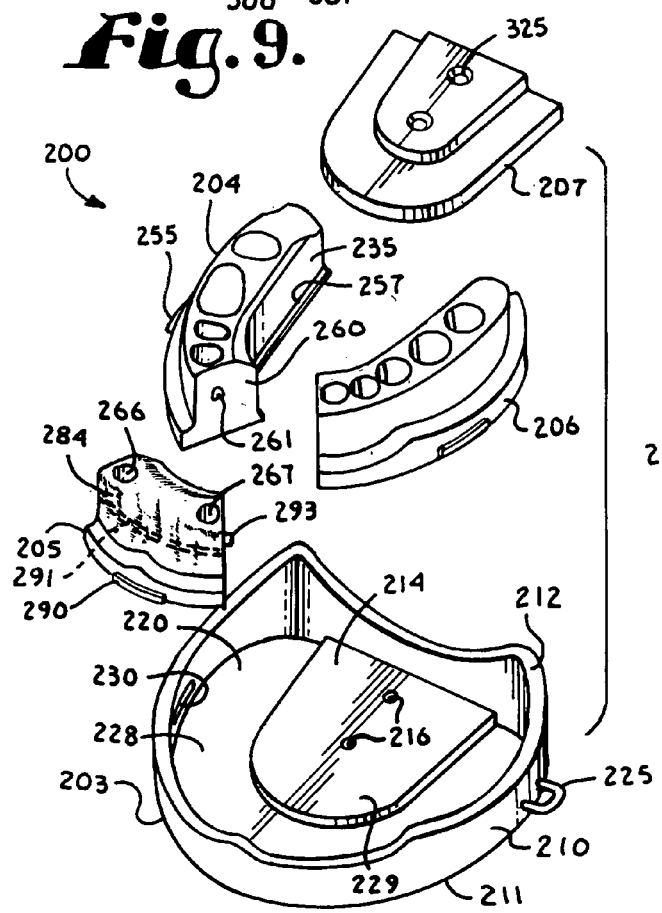

DENTAL TRAINING DEVICE

CROSS REFERENCE TO RELATED APPLICATIONS

The present application is a continuation-in-part of prior U.S. application Ser. No. 10/024,683 filed Dec. 18, 2001 and entitled DENTAL TRAINING DEVICE, now abandoned, which was a continuation-in-part of prior application Ser. No. 09/848,739 filed May 3, 2001 and entitled DENTAL TRAINING DEVICE, now U.S. Pat. No. 6,520,775.

BACKGROUND OF THE INVENTION

The present invention related to dental equipment, and more particularly, to teaching tools for the use of endodontic apical location equipment.

During certain dental procedures, the pulp of the tooth must be removed and other procedures must be performed on the root canal. Persons training to become dentists must learn how to properly remove such pulp and perform the other necessary procedures. Precise location of the root apex is vitally important for the correct endodontic treatment of a tooth. Pulp tissue is richly vascularized and innervated and is contained in the pulp cavity inside the tooth including in the pulp chamber and in pulp canals in tooth roots. The pulp canals are often referred to as root canals. If the endodontic procedure of extracting and cleaning the pulp tissue from a root pulp canal is performed at a length short of the apex, pulp tissue may remain in the canal. Failure to remove all pulp tissue may lead to infection and pain for the patient and necessitate additional surgery. If the endodontic procedure is performed beyond the length of the root apex, the reamer may penetrate into the periodontal ligament leading to pain and extreme sensitivity to the patient. Therefore, current endodontic procedures normally require the careful locating of the root apex at the base of the pulp canal before the reamer or other tools are used to enlarge the pulp canal.

Multiple methods are currently utilized to determine the location of the apex during an endodontic procedure on a live patient. One procedure is the use of x-ray radiographs of the tooth while a metal endodontic reamer is located in the root canal. This allows the dentist to visually compare the length of the metal reamer to the location of the end of the root to determine the location of the root apex. This method is often unreliable and not cost-effective.

A second method is to use an electrically aided apical position location. Certain electronic aids and methods of their use include those described in U.S. Pat. No. 5,759,159 to Masreliez, U.S. Pat. No. 5,211,556 to Kobayashi et al, and U.S. Pat No. 6,059,569 to Otsuka, all incorporated herein by reference. These patents describe apical position locators utilizing impedance measurements to determine the location of the apex that use electrical conductance. In the electrical conductance approach, an electrically-conductive probe is inserted into the root pulp canal and a second electrode is attached to the patient's body, such as by hanging a hook-shaped electrode from the patient's mouth. As the probe is inserted into the root pulp canal and advanced through the root pulp canal to the root apex, the electrical impedance between the probe and the electrode is continuously measured. The electrical impedance is greater when there is little conductance between the probe and the electrode, such as when the probe is in the pulp canal, and lower when there is greater conductance between the probe and the electrode, such as when the probe touches the tissue at the bottom of the pulp canal that is much more conductive than the pulp canal itself. Once the impedance lowers and reaches a predetermined range or value, the location of the apex is indicated and the depth of the probe is noted for future use with other instruments. The electrical approach using impedance for determining apex location is currently the preferred and standard technique used in endodontic practice and taught in dental schools.

Instruction in the use of electrical apical position locators has generally required practice upon live patients in need of endodontic treatment. Performing endodontic procedures on healthy teeth is unethical and represents dental malpractice. Endodontic patients are often in pain prior to seeing the dentist, and are usually apprehensive about the endodontic procedure and less than enthusiastic about serving as subjects in dental instruction on the use of apical position locators. The additional pain which may be encountered, or the mere potential for such additional pain, results in few such patients volunteering to allow students to perform the procedure.

The number of endodontic procedures that a dental student or a doctoral student in general dentistry performs on live patients is severely limited by the number of willing participants in need of such procedures. Dental students and general dentists would benefit from additional training and instruction in the use of apical position locators in a realistic setting. In turn, the endodontic patient would benefit from the additional training received by the practitioner.

Prior to this invention, no adequate surrogate for the live patient has been developed for instruction in the use of electrical apical position locators. U.S. Pat. No. 5,503,562 described a transparent endodontic inspection block which allows the dental student to simulate the cleaning out the root pulp canal. The student utilizing the inspection block could look through the side of the inspection block and locate the root apex. This invention is not designed to train apex location techniques and does not represent realistic conditions of endodontic treatment. U.S. Pat. No. 4,137,633, issued in 1979, disclosed a resilient mass located at the apex of a block of transparent material to simulate the tactile sensation of the periodontal membrane located at the apex of a natural tooth. Thus, prior devices permitted students to visually locate a simulated apex through the addition of a resilient mass located at the apex. However, no known prior devices have disclosed providing a simulation of a live tooth and human tissue to practice using an electrical apical position locator.

Additionally, during training to do such procedures, it is important to have the procedure simulated on an actual patient, as much as possible, so that the student can learn how to overcome problems of working in the patient's mouth. Therefore, it is also desirable to provide a training device that can be utilized for at least some of the student endodontic procedures and which simulates a live patient, as much as possible.

In addition to the need for a training device for use in teaching root canal procedures, it is also desirable to have such a device that can be used to teach other types of procedures such as how to treat dental decay and how to do crown and bridge procedures. Because training devices may be expensive for the student, it is preferable that the device allow the student to practice different types of procedures which preferably require somewhat different structure. Root canal procedures require real or artificial teeth having a root and with structure allowing electrical conductance. Crown and bridge work require a section of teeth wherein one or more is missing and real or artificial teeth can be modified to accept a bridge with a skin like structure over the gum, as it is important for the student to correctly interface the bridge with the skin. Dental decay procedures do not require a root or electrical conductance, but preferably utilizes real or artificial teeth that are mounted in such a manner so as to simulate the interaction of the teeth with each other and with ligament tissue that normally holds such teeth in place. Each of these and other procedures are preferably performed on separate or different practice units to allow the student the best range of training.

Furthermore, it is desirable that the different sections be modular so that a student can preform one, two or all procedures within a single assembly. For example, when working on one procedure, all the individual modular inserts in an assembly may be designed for a single procedure to provide multiple locations to practice or such can be changed to provide modular inserts for multiple procedures for practice or testing. Because the individual modular inserts can be easily changed, when one is used and is not reusable, it can easily be replaced by another without requiring that the entire assembly be discarded.

SUMMARY OF THE INVENTION

The present invention provides an improved device and method for the training of the use of an apical position locator. The invention uses a real or replicated tooth with a root and a root pulp canal (often referred to as a root canal) having an apex at the root tip. Real teeth with pulp in the root canals are available from a supply of such teeth removed from patients for other reasons or from cadavers. In the present invention a student practices on a tooth set in a hard medium which mimics the electrical impedance of human tissue so that an electronic apical locator may be used. In a first embodiment, the tooth is mounted in a single, rigid conductive medium which mimics the conductivity and impedance characteristics of human tissue. An alternative embodiment uses a first highly conductive medium wrapped around the root tip to cover the apex of the tooth which is then surrounded by a second rigid medium so as to set the tooth in a fixture containing the second medium. The second medium may be less conductive and holds the tooth suitably for manipulation training purposes.

An electronic apical position locator has one lead connected to an endodontic probe or reamer and the other to an electrode blade extending from the medium. When the reamer is inserted in the root canal and extended so that the reamer tip contacts the conductive medium at the root apex, the electronic circuit of the apical position locator is closed, the impedance is measured and the apex is appropriately indicated by the apical position locator.

In another embodiment of this invention, the tooth is mounted in a manikin jaw that simulates a working human jaw. Preferably, the manikin jaw has sockets at various locations that are located whereat various teeth would normally be found. Each tooth upon which the student is to train is mounted in an electrically conductive medium that has a lower impedance than the training tooth root canal and which desirably has approximately the conductance or impedance of tissue found around the natural live root apex. A highly conductive medium is preferably placed in a protective sleeve and a second medium or matrix is placed about the tooth within a sleeve and then allowed to harden. The sleeve is sized and shaped to be received in one or more of the sockets. Preferably, the sleeve is held in place by a pin, such as a thumbscrew or similar fastener, that also acts as an electrical conductor in contact with the conductive material in the sleeve and in turn is electrically connected to an electrode of an apex location apparatus. The entire matrix may be a highly conductive medium or a less conductive medium may be used externally relative to the sleeve. Further, if the pin connects directly with the highly conductive medium in the sleeve, the remainder of the matrix does not have to be conductive.

A more detailed understanding of the invention will be obtained from the following description of the preferred embodiments taken in conjunction with the attached drawings.

This invention provides an actual or replicated human tooth with an electrically equivalent replicated human tissue medium, especially in a human form manikin, to provide a realistic simulator for training in the use of an electrical apical position locator. Patient volunteers do not normally clamor for dentists-in-training to practice root canals upon them, so this invention allows the dental student the opportunity to practice in a realistic environment, preferably with real teeth having-pulp in the root canals thereof. The user may select a partially radiopaque electrically conductive medium, which allows the student to also simulate the determination of the location of the root apex through the use of an x-ray radiograph.

In yet another modification of the invention, the training aid is provided with modular inserts that mimic various portions of the jaw and which can be easily exchanged with other inserts that mimic the same portion of the jaw. In this manner, the inserts can include one or more units for training for particular procedures such that all of the assembled inserts may be for the same procedure or for different procedures. Each insert can be easily replaced by another for the same or a different procedure.

Different inserts may be advantageous for many different procedures. For example, the inserts may be especially designed to act as an instruction aid for root canal procedures, repair of dental decay procedures, for crown and bridge procedures or for other procedures. The root canal procedure inserts are preferably of the type described above with the added feature of providing a common electrical conductor for the entire insert support structure so that electrical conductance will be available whether none, one or multiple inserts are for root canal procedures. The dental decay procedure inserts preferably include structure to allow teeth to be mounted in a matrix that mimics the setting of live teeth relative to ligaments that support and hold live teeth, so the student more closely encounters the feel of working on live teeth, especially crowding by adjacent teeth and flexing under pressure. The crown and bridge procedure inserts preferably include an artificial skin layer that mimics a patent's skin, so that the student gains experience in mounting crowns and bridge relative to skin tissue.

OBJECTS AND ADVANTAGES OF THE INVENTION

Therefore, the objects of the present invention are: to provide a training aid for dental students comprising a holder or fixture for holding a tooth in a solid medium or material that is at least in part approximately as electrically conductive as non-boney tissue found in humans that surrounds teeth so as to simulate the electrical conductivity or impedance found in such tissue and thereby allowing a student to perform practice root canal procedures, including practice with an electrical apical position locator, without need for living patients; to provide such a training aid wherein the fixture is an independent container partially filled with solid electrically conductive medium or material that simulates the electrical conductivity or impedance of human tissue surrounding teeth; to provide an alternative embodiment of such a training aid wherein the fixture includes a socket in a manikin that simulates a human jaw structure; to provide such a training aid wherein the sleeve is sized and shaped to fit in such a manikin socket to allow easy removal and cleaning after the training session is complete; to provide an alternative manikin-training aid wherein teeth with a highly conductive media about the root tips thereof are molded directly into the manikin; to provide such a training aid wherein a thumbscrew is used as a pin to secure such a sleeve in a socket and wherein the thumbscrew also functions as an electrode for the apical position locator; to provide such a training aid that includes a set of modular training inserts wherein such inserts can be exchanged for similar or different inserts to form a training assembly; to provide such a training aid that provides such inserts wherein each insert is especially adapted to particular procedures, such as treatment of dental decay procedures, root canal procedures and crown and bridge procedures; to provide such training aid wherein all of the inserts in a final assembly may be selected for training on the same procedure or for different procedures to meet the needs of the student using the training aid; to provide a method of training aspiring dentists in endodontic procedures using the aforementioned training aids such that the students become skilled without having to practice on live patients; and to provide such training aids that are easy to use, comparatively inexpensive to make and especially well suited for the intended purpose thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 5 is an enlarged cross-sectional view of a sleeve, tooth and highly conductive medium during a first step in assembly of the second alternative training aid.

FIG. 6 is an enlarged cross-sectional view showing a second step subsequent to the first step shown in FIG. 5 in the assembly of the second alternative training aid.

FIG. 7 is an enlarged cross-sectional view of the second alternative training aid showing a third step in assembly thereof.

FIG. 9 is an exploded perspective view of a third modified training aid according to the present invention having a plurality of modular inserts wherein each insert is utilized for training a student with respect to a different dental procedure.

FIG. 10 is a perspective view of the third modified training aid with inserts assembled.

FIG. 12 is a fragmentary cross-sectional view of the third modified training aid, taken along line 12—12 of FIG. 10.

FIG. 13 is a fragmentary cross-sectional view of the third modified training aid, taken along line 13—13 of FIG. 10.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

First and Second Embodiments

Figure 1:
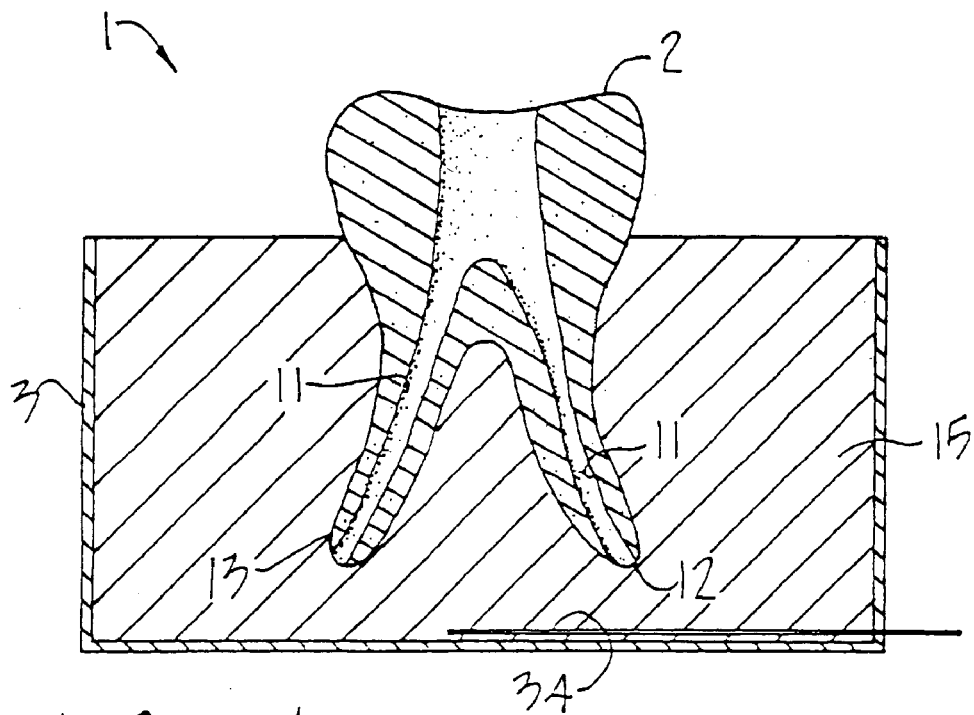
FIG. 1 is a cross-sectional view of a training aid in accordance with the present invention.

Referring to FIG. 1, the reference numeral 1 generally indicates a training device according to the present invention which is useful to create an effective simulation of a tooth in a patient, so that a student may practice using an electronic apical position locator. The training device 1 consists of a tooth 2 which may be an extracted human tooth or a replica, which is set in a fixture 3 and connected to an apical position locator 4, FIG. 3, as hereinafter described. In more detail, an illustrated exemplary tooth 2 is a pre-molar with two roots 10, each with a root canal 11 ending at an apex 12 near the tip 13 of each root. Other tooth forms are equally suitable. In a live tooth, the root canal 11 is filled with nerve pulp tissue. Also, a live tooth is set into a periodontal ligament which surrounds the root 10 and acts as a barrier between the tooth root and the bone that holds the tooth. In a patient the periodontal ligament or tissue around the tooth is moist and electrically more conductive than the tooth, thereby enabling the use of an electronic apical position locator 4 which relies on the measurement of impedance to determine when the more conductive tissue is encountered and therefore when the apex is reached. When the measuring probe electrode approaches the apex, the magnitude of impedance or the phase angle of the impedance between the measuring probe and oral probe electrode starts to change. The detector identifies the apex when the designated range or the frequency of impedance is reached.

In the illustrated example, the tooth 2 is a "dead" tooth which has been extracted from a patient or cadaver and is not supported by a living periodontal ligament or other live conductive materials. As shown in FIG. 1, the tooth 2 is set in a container or fixture 3 which is selected for ease of manipulation by a student. Preferably, a single setting material 15 is selected which provides sufficient rigidity to support the tooth 2 during handling and during the practice of root canal procedures. Ideally, the selected material 15 should also replicate the range of impedance of live human tissue in order to provide an impedance in the range of the apex locator setting. Since there are many different types of apex locators on the market, a single conductive material having an impedance not in the range of live human tissue can also be used for some apex locators of simple design and it is foreseen that a conductive material could be selected for a specific locator. Generally, the selected material 15 should replicate the conductivity of live human tissue in order to provide an impedance generally matched to the impedance of live tissue. Because an electric apex locator of advanced design contains circuitry and components to measure the impedance of human tissue and then compare the impedance value to the impedance values obtained by a measuring electrode inserted into the root canal, a closer match of impedance between the material 15 and the circuit of the apical locator 4 in the locating of apex is normally preferred. A suitable range for the volume resistivity of the medium 15, 20 and 22 supporting the tooth 2 in the fixture 3 is in the range from $10^{15}$ to $10^{-3}$ ohm/cm.

To obtain a suitable support medium, conductive material is mixed with different binders. Such a binder can be plastic resin, polymer resin, plaster, stone, clay etc. Various types and concentrations of conductive materials in the binder have been conceived and include carbon, carbon fiber, graphite, silver powder, metal or metal coated fiber or powder or flakes, silicon, silicon dioxide, germanium, selenium, conductive polymer and others in slight to significant concentrations. If a radiopaque support medium can be tolerated, then a high metallic content or radiopaque chemical such as barium sulfate or stainless steel fibers or powder are usable with a binder. If radio transparency is needed, then metallic content is limited and carbon or other non radiopaque materials are increased to a proportion balancing strength, conductivity and human tissue impedance. The attribute of impedance matching is intended to bring impedance values into a range sensed by the circuit of the electronic apex locator.

Figure 2:
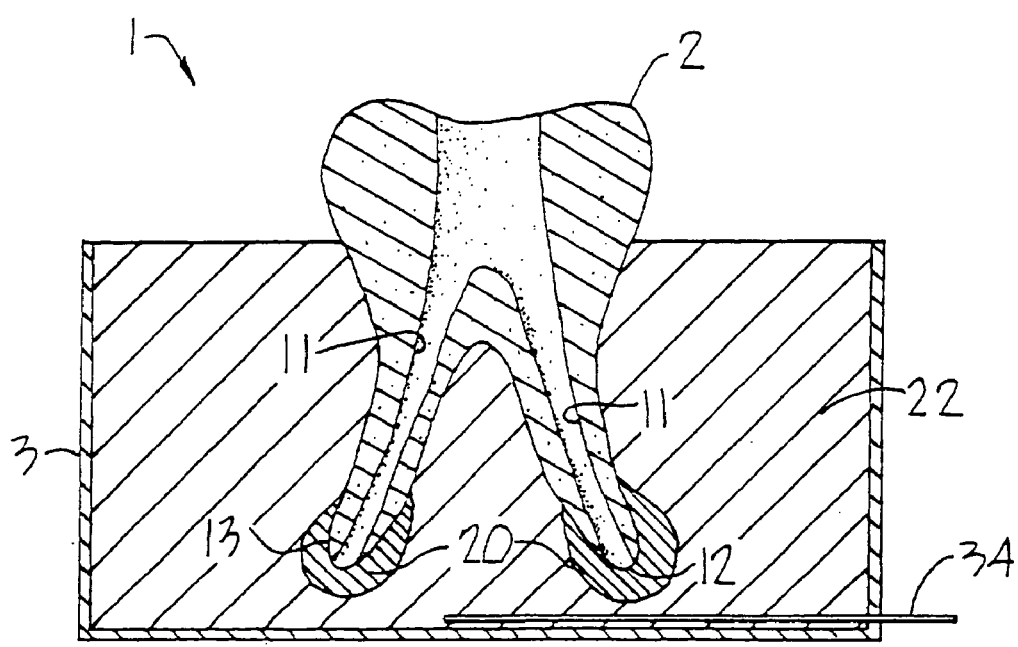
FIG. 2 is a cross-sectional view of a first alternative training aid.
Figure 3:
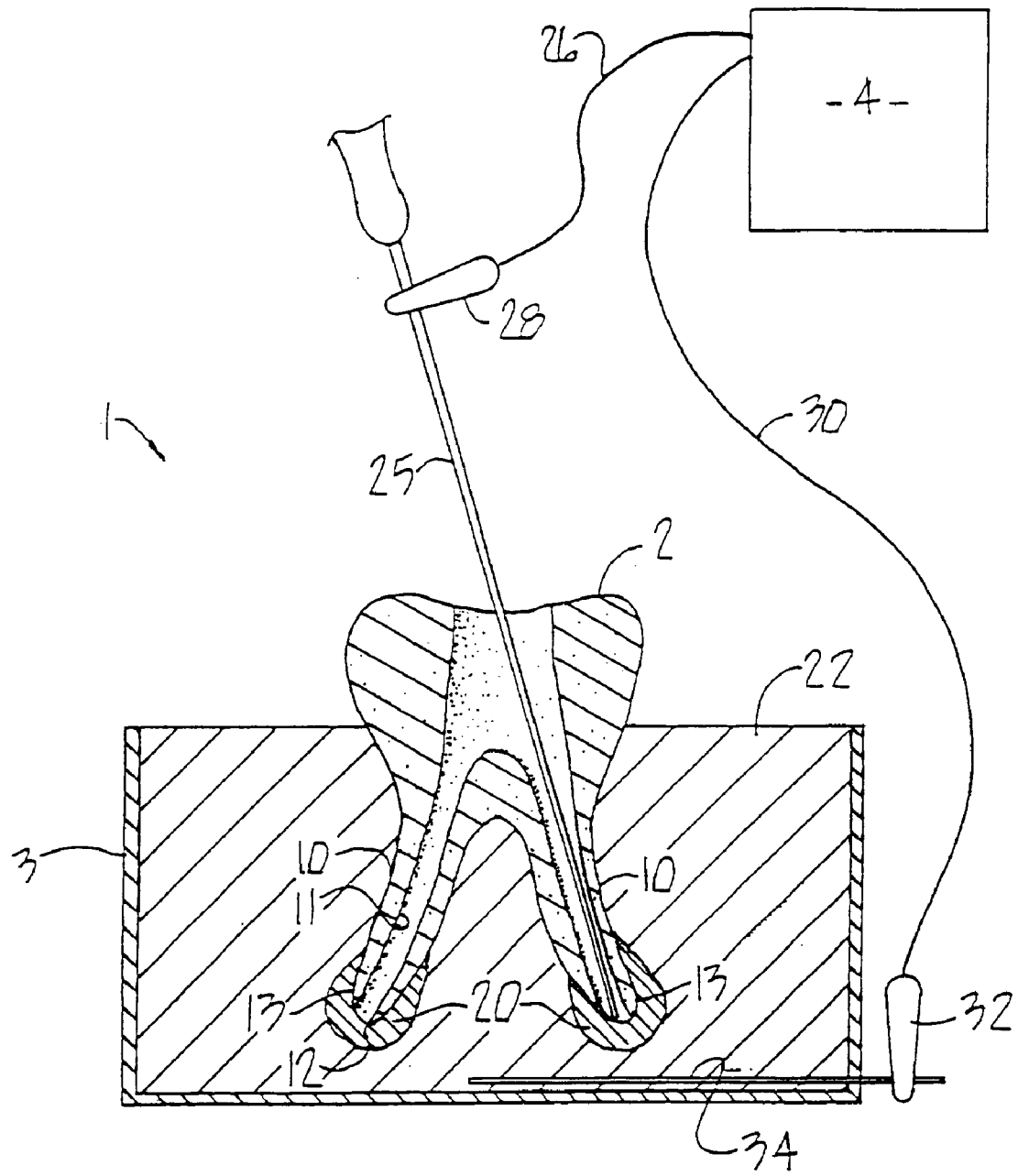
FIG. 3 is a cross-sectional view of the first alternative embodiment of the training aid shown in connection with an electronic apex locator.

A second embodiment of the present invention is shown in FIGS. 2 and 3 and uses two conductive medium components. The second embodiment is essentially the same as the first embodiment described above except for a modification to the medium supporting the tooth and is thus numbered the same except for this medium. In particular, in the second embodiment, a first conductive medium 20 is applied to the root tip 13 to cover the apex 12, generally in a ball about the root tip 13. When applying the first conductive medium 20 to the root tip 13, care is exercised so as not to pack the medium 20 into the canal 11, but to merely cover the apex 12 as it intersects with the root 10. The preferred material of the first conductive medium 20 is a water based or a highly conductive material. The first conductive material or medium 20 can be a mixture of water, alginate, agar, gum, clay or a highly concentrated carbon or metal powder that is a very good electrical conductor in plastics, especially acrylics, or a mixture with a calcium or sodium inorganic salt, such as calcium sulfate.

The tooth with its root tip coated with the first conductive medium is placed in a second conductive medium 22 which fills the fixture 3 and which is initially soft or even liquid. The second conductive medium 22 is preferably then set or hardened to form a solid support for the tooth 2. Settling can be accomplished by allowing the medium to dry, where appropriate, allowing it to chemically set such as an epoxy or acrylic, heat setting the medium 22, where it is capable of being heat set, or the like. The second medium 22 is preferably mixed with a conductive element as mentioned before, typically a resin type material, so that it can hold the tooth 2 in place for handling and practicing root canal procedures, after being hardened or set.

The first conductive medium 20 and the second conductive medium 22 may possess radiopaque material, if training utilizes radiographs to simulate use in a real patient. Such radiopaque material may include material such as metal fibers, metal-coated fibers, carbonaceous material, metallized glass or barium sulfate, as a substantial component of the medium 22 in sufficient amount to produce radiopaqueness. The first conductive medium 20 and the second conductive medium 22 may possess materials of differing radiopacity to simulate the different radiopacity of the periodontal ligament and the bone in a patient.

FIG. 3 shows the training device 1 in connection with an apical position locator 4. To enable the training device 1 to be utilized with the apical position locator 4, a measuring probe such as an endodontic reamer 25 is connected to the apical position locator 4 via leads 26 and a connector, such as an alligator clip 28. The apical position locator 4 is connected to the conductive medium such as the second conductive medium 22 via lead 30 and a connector such as an alligator clip 32, connected to an electrode or probe 34 set in second conductive medium 22. In the illustrated example, apical position locator 4 indicates the closure of an electronic circuit when the endodontic reamer 25 contacts or almost reaches the conductive medium 20 at the apex 12. Then the resistance or impedance of these materials are measured, compared and calculated based on the pre-set formula in the apex locator. A final reading will indicate reaching the apex by the tip of the dental reamer. Normally, the apical position locator possesses sufficient sensitivity that it can determine the distance between the tip of the endodontic reamer 25 and the apex 12 and the locator provides a visual readout of that distance.

In the practice of the invention, a tooth such as an extracted human tooth 2 is used to train a user by placing the tooth 2 into a container or fixture 3 and supporting the tooth 2 therein by a conductive medium, such as the single medium 15 shown in FIG. 1. Alternatively, a first conductive medium 20 can be molded around the root tip 13, being careful not to enter the canal 11. Next, the tooth 2 with first conductive medium 20 wrapped around the root 10 is placed in second conductive medium 22 in the fixture 3. The second conductive medium 22 is allowed to set so that it firmly holds tooth 2 in place. The apical position locator 4 is connected to the endodontic reamer 25 and the probe 34 so that when the reamer 25 is placed in the root canal 11 and the reamer tip contacts the first conductive medium 20 or single medium 15 (FIG. 1) at the apex 12, the locator electronic circuit completes the measurement of electronic resistance or impedance and the apical position locator 4 so indicates. Importantly, the resistance of the conductive medium is selected so that the electronic apical locator measures the resistance.

Optionally, the training device may be utilized along with x-ray machines and radiographic film to simulate the verification of the location of the apex 12 through simulation of the relative radiopacity of the periodontal ligament and bone by utilizing differing levels of radiopaque materials in the first conductive medium 20 and the second conductive medium 22.

Various forms of conductive media may be used as desired including thermoplastic resins, acrylic, polymers and plasters with fillers such as carbonaceous material or metal fibers or flakes.

Third Embodiment

Illustrated in FIGS. 4 through 8 is a third embodiment of a dental training device in accordance with the present invention that is generally represented by the reference numeral 100. The training device 100 has certain aspects that are similar to the devices that are illustrated and disclosed in the previous embodiments and reference is made to those embodiments for certain details such as materials of construction.

The training device 100 generally comprises a manikin 110 having at least one socket 111 and, unlike the previously disclosed embodiments, includes a sleeve 112 operably received in the socket 111 and within which a tooth 113 is mounted in a generally solid matrix 114.

The manikin 110 is preferably a type of device which is sometimes also referred to as a typodent that is utilized in the training of dental students. The manikin 110 has an upper jaw or maxilla 120 and a lower jaw or mandible 121 that are mounted on a support frame 122, such that the jaw 120 can be articulated with respect to the jaw 121 in a manner that is similar to that of a human jaw, so as to simulate a human jaw for purposes of training of a dental student. The jaws 120 and 121 have a plurality of real and/or simulated teeth 126 that are positioned about the facing surfaces of the jaws 120 and 121 in such a manner as to simulate the appearance of teeth in a typical human dental patient. The jaws 120 and 121 are constructed of a material that can vary, depending upon what is desired to be taught to the students, but which is typically a rigid or semi-rigid plastic that has the shape and appearance of the gums and mouth of a human.

Figure 4:
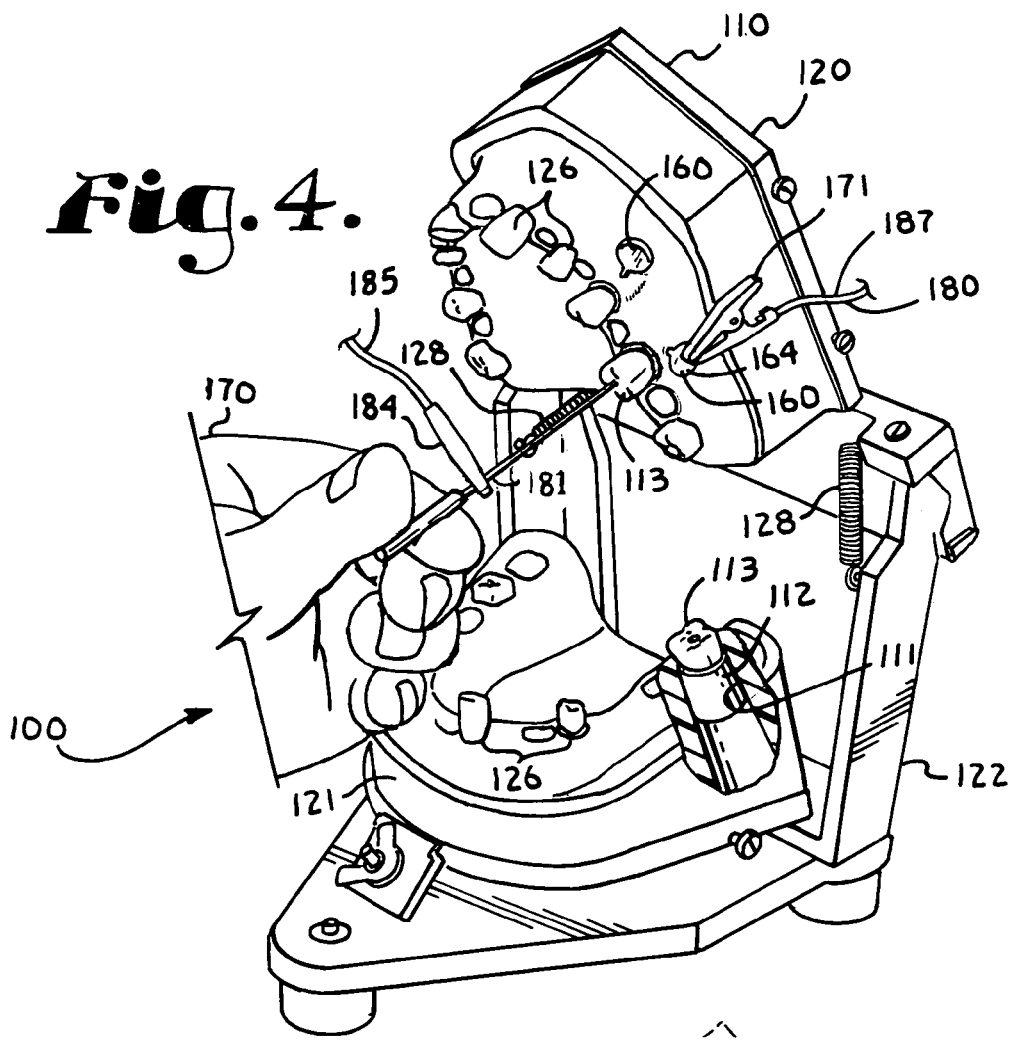
FIG. 4 is a perspective view of a second alternative training aid in accordance with the present invention, illustrating a training procedure being performed and with portions broken away to show internal detail thereof.

As will be discussed below, the material of construction of the jaws 120 and 121 may in some cases be an electrically conductive material that has conductivity quite similar to the gums and mouth tissue of a human patient or may alternatively be constructed of a non-conductive material. The material of construction of the jaws may also be radiolucent or radiopaque depending on whether x-ray procedures are to be used. As is seen in FIG. 4, the upper jaw 120 of the present embodiment is hinged on the support frame 122 and is biased to a closed position by springs 128 wherein the teeth 126 of the upper jaw 120 engage similar teeth of the lower jaw 121. This simulates a patient with a mouth that can be opened and in which a student must work to perform procedures using the device 100.

The sockets 111 are provided in the jaws 120 and 121 at locations where it is desirable to provide training to a student learning endodontic procedures. In the illustrated embodiment such sockets 111 are provided in the lower jaw near the rear where a large molar would be normally located and which is illustrated by broken away portions in FIG. 4. Sockets 111 are also provided in other locations such as are illustrated in the upper jaw 120 where somewhat more forward teeth are normally located. A training procedure is illustrated in FIGS. 4 to 8 with respect to an upper jaw socket 111, such as is shown in FIG. 4. Each socket 111 is sized and shaped to receive a sleeve 112 snugly therein. Each of the sockets 111 has a shape that is somewhat in the form of a hollow truncated cone and is accessible from the rear of each jaw 120 and 121 opposite the teeth 126 (see FIG. 4).

As is best shown in FIGS. 5 through 7, each sleeve 112 has a general truncated conical shape with a thin wall 129 and has a hollow interior so as to form a cavity 130 with an open upper end 131 and open lower end 132. The cavity 130 has an interior surface 133. The sleeve 112 is sized and shaped to receive a tooth 113 and combined form an insert 134. Such an insert 134 is shown in phantom lines in FIG. 8 prior to placement in the socket 111 wherein the insert is shown in solid lines.

As has been described with the previous embodiments, the tooth 113 is preferably a human tooth that has been removed from a live patient for some other reason or is a tooth that has been harvested from a cadaver. In certain instances where a human tooth is unavailable, an artificial tooth that is sized and shaped to mimic a real tooth may be used. Such a tooth 113 includes a pulp chamber 137 and at least one root pulp canal or root canal 138 that extends along each root 139 of the tooth 113. Normally, such a tooth 113 would include pulp 141 intact in the root canals 138 and pulp chamber 137. The root canals 138 containing the pulp 141 extend to an apex or tip 143 of each root 139.

The practice tooth 113 extends outwardly from the sleeve 112 such that a crown 146 of the tooth 113 is exposed and the tooth roots 139 are located within the sleeve 112. The tooth 113 is snugly and rigidly held in its associated sleeve 112 by the matrix 114. In the present embodiment, the matrix 114 has two components 148 and 150.

The first matrix component is a relatively good electrical conductor that is chosen to simulate the electrical conduction found in human tissue in the ligament and gum surrounding a live human tooth. The highly conductive matrix component 148 can be any of the materials that have been discussed in the previous embodiments for such a component.

In the present embodiment the highly conductive component 148 is a malleable or semi-solid material that is molded about each root tip 143. Because the material is soft and can be stripped from the root 139 accidentally, a protector 149 is placed over the highly conductive component 148. In the present embodiment the protectors are annular sleeves 151 that are placed over each tooth root 139, as is shown in FIGS. 5 and 6. The highly conductive component 148 is specifically designed to provide good conductance at each root tip 143. Each sleeve 151 is manually snugged against a respective root 139 and about the highly conductive component 148 to hold the latter in touch with a respective root tip 143. It is foreseen that other forms and shapes could be utilized for the highly conductive component 148 such as a cup or the like and without a protector.

The second component 150 of the matrix 114 can be several different types of materials depending on whether or not it is desired for the component 150 to also be highly conductive or for conduction to be transferred from the highly conductive component 148 to the locating device described below through some other structure. Consequently, it is foreseen that the matrix component 150 can either be a highly conductive material similar to that of component 148, a semi-high conductive material that would be useful in providing conduction between the component 148 and a locator or alternatively, may not be conductive at all.

It is important that the matrix component 150 be at least semi-solid and preferably rigid during usage of the device 1, so as to support the tooth 113 in position while procedures are being performed on the tooth 113. For this purpose, various thermally set materials or the like could be utilized wherein the component 150 is initially a resin or powder into which the tooth 113 can be initially pushed or embedded after which the component 150 is heat set and solidified. Alternatively the matrix component 150 may be a stick-type resin that forms a liquid when heated and which can be dispersed into the sleeve 112, such as is illustrated in FIG. 7, and thereafter allowed to harden by drying, chemical reaction, heating with subsequent cooling or the like. It is foreseen that other types of matrix components may be used in accordance with the invention. For the purpose of dispersion, a heating gun 155, such as a glue gun, distributes drops or a stream of conductive liquid or gel material 156 into the sleeve 112 around the tooth roots 139 which thereafter solidifies or hardens as matrix component 150.

A pin 160 is utilized to secure the sleeve 112 in a respective socket 111. While it is foreseen that in some instances, the matrix 114 could be placed in a socket directly without a sleeve 112, such a sleeve 112 is preferred as same allows for quick change out and reduces the time that would otherwise be required to clean the hardened matrix out of the socket.

Figure 8:
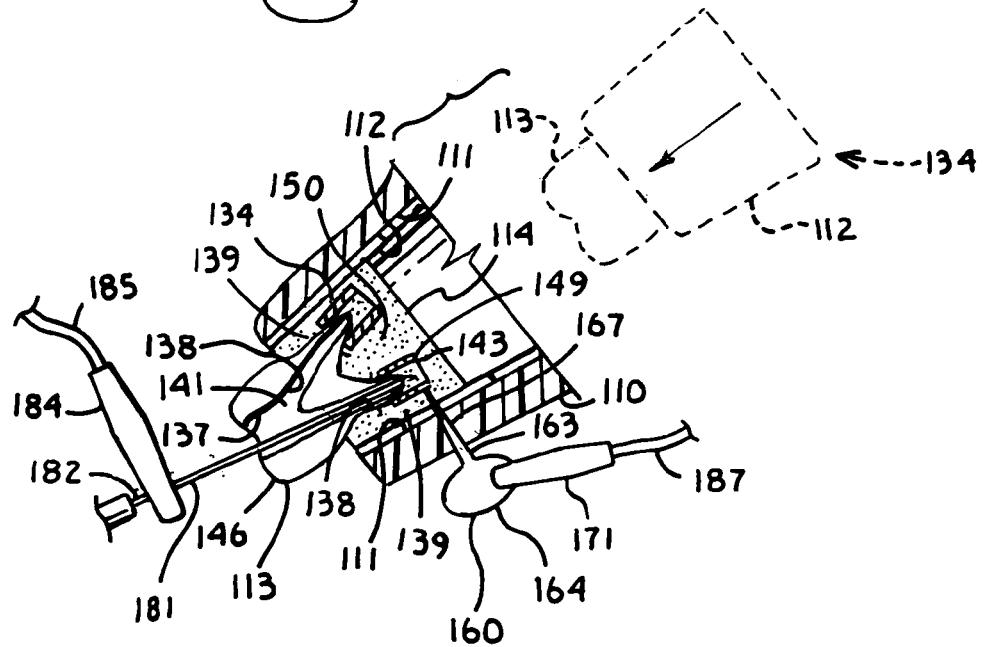
FIG. 8 is an enlarged cross-sectional view of the second alternative training aid fully assembled and shown in a fragmentary manikin as shown in FIG. 4.

The illustrated pin 160 is a thumb screw that has a threaded shank 163 and flat head 164. The pin 160 is received through openings 167 in the manikin jaws 120 or 121, as is shown in FIGS. 4 and 8. The threaded shank 163 provides two functions. In particular, the shank 163 locks the sleeve 112 in position relative to a respective socket 111 and also provides a metallic conductor that directly engages the highly conductive component 148 when assembled, as shown in FIG. 8. The head 164 also provides two functions. The head 164 allows a grasping structure for a user to insert the pin 160 and further provides a surface that is comparatively shaped to receive an alligator clip 171, as will be discussed below.

It is foreseen that the tooth 113 can be inserted into the matrix 114 in the sleeve 112 in a number of ways, but one alternative is shown in FIGS. 5 to 7. In particular, the crown 146 of the tooth 113 to be mounted is placed in an indentation 173 in a block 174 of wood, embedded in a putty-like material, or the like. The highly conductive matrix component 148 is placed over the root tips 139 and thereafter the root sleeves 149 are placed over the tooth roots 139 and the component 148. Then the matrix holding sleeve 112 is placed over the lower part of the tooth 113 with the sleeve lower end 132 engaging an upper surface 175 of the block 174. The liquid material 156 that forms the second matrix component 150 is then deposited in the sleeve 112 so as to preferably cover the root tips 143, the conductive component 148 and the protectors 149, so as to secure the tooth 113 in the sleeve 112. The sleeve 112 with the tooth 113 secured therein is then placed in a selected socket 111 and the pin 160 is used to secure the sleeve 112 in the socket 111. The pin 160 preferably also touches a respective highly conductive component 148 in which case the remainder of the matrix 114 that is component 150 does not have to be electrically conductive. If the pin 160 is not positioned to touch the highly conductive component 148, then the matrix component 150 must also be electrically conductive.

After the sleeve 112 is placed in the socket 111, a student 170 connects an apical position locator 180 to the device 100. In particular the student 170 uses an elongate reamer or probe 181 that has a shaft 182 sized to extend through a selected root canal 138. The shaft 182 is a conductive metal and is electrically joined by an alligator clip 184 attached to a lead 185 or the like to the main body (not shown) of the locator 180. The alligator clip 171 with a lead 187 is attached to the pin head 164, as is seen in FIG. 4. After opening the tooth crowns 164 by a well known process, the student then practices finding the bottom of the root canal 138 in the manner previously described. In an endodontic procedure, the finding of the apex of the root canal 138 is accompanied by removal of the pulp 141 and enlargement of the pulp or root canal 138 to the depth determined by the above described procedure. Thereafter, subsequent root canal procedures are performed.

It is foreseen that when a patient has a tooth that has a metallic filling or crown extending into or near the pulp chamber or root canal, it may be necessary to use a probe that is insulated over at least the portion of the shaft that would engage the filling or crown. For this purpose part of the shaft may be coated with nonconductive material. It is also foreseen that a hook, eye or the like may be joined to and extend-outward from the probe shaft to facilitate connection of the locator device and especially an alligator clip.

It is also foreseen the manikin may be constructed of conductive material as well as the entire matrix 114 in which case it is not necessary that the pin be conductive, but only that the locator lead hook onto or otherwise join with the manikin jaw somewhere therealong. It is also foreseen that the sleeve holding the tooth may be held in place by something other than a pin or set screw. For example, a cover hinged to the manikin or a moveable hook could be used to hold the sleeve in the manikin during training procedures.

It is foreseen that the highly conductive material may include a filler of conductive carbonaceous material, including furnace black, channel black, acetylene black, graphite fiber and carbon fiber; conductive fiber materials, including aluminum, nickel, copper, iron and stainless steel fibers; and metal coated fibers, including metallized glass, metallized graphite and metallized plastic fibers; conductive metal powders, including metallic flakes, powder and milled or ground metallized glass; and other conductive materials, including conductive organic polymers, glues, sponges, epoxies, paints, alginates and the like. A binder for the highly conductive component may be chosen from thermoplastic resins, including acrylic, polyvinyl chloride, polypropylene, polyethylene terephthalate, polystyrene, abs (acrylonitrite butodiene styrene resin), polyphenylene ether, polycarbonate, styrene and ethylene vinyl acetate; polymers, including bis-gma, TEGAMA and HEMA; and others, including plasters, yellow stone, clay and the like.

The following radiopaque materials may be added to some embodiments: barium sulfate and substantial concentrations of metal fillers such as nickel, stainless steel and the like.

It is foreseen that a conductive portion of the tooth holding matrix can also be a mixture of conductive materials including water, glycerine and other conductors, especially a percentage of from about 1 to 80% by weight in combination with a filler or gelatin selected from clay, silica, gum, agar, alginate and the like. Further, the conductive material is preferably water with sodium hypochlorite, EDTA (ethylenediaminetetraacetic acid), conductive aluminum compounds, conductive calcium and sodium salts, conductive carbonate compounds, conductive basic compounds and the like in a range from 1 to 80% by weight with the remainder being binder or miscellaneous fill.

The following examples are provided to illustrate the invention and are not intended to be limiting on the scope or interpretation of the claims:

EXAMPLE I

Highly conductive matrix components were produced in accordance with the invention having the following formulation by weight:

| Composition A | |
|---|---|
| ethylene vinyl acetate | 68% |
| carbon powder | 30% |
| steel fiber | 2% |

| Composition B | |
|---|---|
| flour | 45% |
| salt | 15% |
| water | 35% |
| oil | 5% |

The highly conductive matrix component Composition B was applied to roots of these teeth, as is shown in FIG. 5 and a root sleeve of plastic tubing was placed about Composition B, as is shown in FIG. 6. Composition A was then placed about the tooth root in a sleeve, such as sleeve 112, as is shown in FIG. 7, and a procedure was performed using an apex locator as described in the last embodiment to find the distance from the crown to each tooth root apex. Two other procedures were performed on each of the teeth to determine root length which were by x-ray measurement and by in vitro measurement. The results are provided in Table 1.

TABLE I

Test Result:

| | Root length in vitro in mm | Root length by x-ray in mm | Root length by apex locator in mm |
|---|---|---|---|
| Anterior teeth | 23 | 23 | 23 |
| Two root bicuspid | 20, 20 | 20, 20 | 20, 20 |
| Three root molar | 19, 19, 19 | 19, 19, 19 | 19, 19, 19 |

EXAMPLE II

Matrix conductive components of compositions C and D were prepared and tests were performed in the same manner as in Example I. The Composition D was applied directly to each root apex and the Composition C was used to surround and support each tooth and around Composition D.

| Composition C | |
|---|---|
| Clay | 70% |
| Carbon-coated fiber | 30% |

| Composition D | |
|---|---|
| Agar | 30% |
| Salt | 10% |
| Water | 55% |
| Oil | 5% |

Table II illustrates the results of testing:

TABLE II

| | Root length in vitro in mm | Root length by x-ray in mm | Root length by apex locator in mm |
|---|---|---|---|
| Anterior teeth | 23 | 23 | 23 |
| Two root bicuspid | 20, 20 | 20, 20 | 20, 20 |
| Three root molar | 19, 19, 19 | 19, 19, 19 | 19, 19, 19 |

EXAMPLE III

Matrix conductive components of compositions E and F were prepared and tests were performed in the same manner as in Example I. The Composition D was applied directly to each root apex and the Composition E was used to surround and support each tooth and around Composition F.

| Composition E | |
|---|---|
| acrylic | 70% |
| carbon powder | 30% |

| Composition F | |
|---|---|
| Gum | 30% |
| Salt | 15% |
| Water | 50% |
| Oil | 5% |

TABLE III

| | Root length in vitro in mm | Root length by x-ray in mm | Root length by apex locator in mm |
|---|---|---|---|
| Anterior teeth | 23 | 23 | 23 |
| Two root bicuspid | 20, 20 | 20, 20 | 20, 20 |
| Three root molar | 19, 19, 19 | 19, 19, 19 | 19, 19, 19 |

EXAMPLE IV

Matrix conductive components of compositions G and H were prepared and tests were performed in the same manner as in Example I. The Composition H was applied directly to each root apex and the Composition G was used to surround and support each tooth and around Composition H.

| Composition G | |
|---|---|
| epoxy | 70% |
| conductive sponge | 30% |

| Composition H | |
|---|---|
| Glycerine | 77% |
| Salt | 5% |
| Water | 15% |
| Carbopol | 3% |

TABLE IV

| | Root length in vitro in mm | Root length by x-ray in mm | Root length by apex locator in mm |
|---|---|---|---|
| Anterior teeth | 23 | 23 | 23 |
| Two root bicuspid | 20, 20 | 20, 20 | 20, 20 |
| Three root molar | 19, 19, 19 | 19, 19, 19 | 19, 19, 19 |

| Composition I | |
|---|---|
| Ground Stone | 60% |
| Carbon Powder | 40% |

| Composition J | |
|---|---|
| Alginate | 60% |
| Water | 40% |

TABLE V

| | Root length in vitro in mm | Root length by x-ray in mm | Root length by apex locator in mm |
|---|---|---|---|
| Anterior teeth | 23 | 23 | 23 |
| Two root bicuspid | 20, 20 | 20, 20 | 20, 20 |
| Three root molar | 19, 19, 19 | 19, 19, 19 | 19, 19, 19 |

The test results for each of the Examples I to V indicate that locating root length apexes utilizing devices in accordance with the invention have essentially the same accuracy as direct measurement (which cannot be accomplished in a living patient) and x-ray.

It is foreseen that teeth may be imbedded in the matrix by several different methods. The matrix can initially be powder, soft, pliable or the like and the tooth pushed into the matrix. The matrix may be poured about the tooth as seen in the third embodiment. Furthermore, it is foreseen that the highly conductive component of the matrix may be located only about the tooth root and surrounded by a second component or the highly conductive component may completely fill a sleeve sized for insertion in a socket or a container, or the highly conductive component may be a layer having less conductive material above and/or below the highly conductive component, including a thin layer of matrix fixing material that forms a substantially solid layer of matrix near the top of the tooth.

As will be apparent to persons skilled in the art, various additional modifications, adaptations and variations of the foregoing specifically disclosed embodiment and method for training in the use of an apical position locator may be made without departing from the objectives and scope of the present invention. Various modifications and changes may be made to the embodiment disclosed herein by those skilled in the art and such are contemplated by the present invention and are to be understood as included within the spirit and scope of the appended claims.

Fourth Embodiment

Illustrated in FIGS. 10 through 13 is a fourth embodiment of a dental training aid in accordance with the present invention and generally indicated by the reference numeral 200. The fourth embodiment includes elements of the first three and reference is made to the first three embodiments for greater detail.

The dental training device 200 includes a tray or structural support 203, three training inserts 204, 205 and 206 and a securing plate 207.

The structural support 203 is generally in the shape of a human jaw and in conjunction with the inserts 204, 205 and 206 provides a user with the feel of working on a human. It can be either an upper or lower portion of the mouth and can be used separately or in combination with a second unit in a manikin of the type shown in FIG. 4.

The support 203 includes a peripheral wall 210 extending upward from a lower and generally flat base 211 to a contoured end 212. A central and rearward portion 214 of the base 211 extends upwardly and has a pair of spaced and threaded bores 216 that extend downward vertically from a top thereof. The remainder of the base 211 is covered by a relatively thin metal conductive plate 220 that is somewhat crescent or horseshoe in shape and which preferably receives all of the training inserts 204, 205 and 206 thereon in touching relationship. The plate 220 includes a metal conductive ring 225 that extends through and protrudes outwardly from the support 203. The plate 220 has an upper surface 228 that is below an upper surface 229 of the base portion 214.

The support wall 210 has an interior facing aperture or slot 230 for each insert 204, 205 and 206 that also face the inserts 204, 205 and 206 respectively when placed on the support 203 and which are used for securing the inserts 204, 205 and 206 in the support wall 210 as described below.

The present embodiment includes three inserts 204, 205 and 206 although it is foreseen that two or more than three could be used in accordance with the invention. The illustrated inserts 204, 205 and 206 are designed to provide practice and instruction to a student training in dental procedures.

In the present embodiment, insert 204 is especially designed for training in repair of tooth decay procedures, insert 205 is designed for training in crown and bridge procedures and insert 206 is designed for training in root canal procedures. Each of the inserts 204, 205 and 206 are modular and can be replaced with other units that provide training for the same or different procedures. In this manner, the student can acquire inserts for a single aid 200 device that can be used multiple times to teach different procedures and can be assembled in such a manner, as shown, to allow training or testing on multiple procedures at the same time or a plurality of training sites for a single procedure. In particular, in some uses, all of the inserts may be for the same procedures.

The insert 204 includes a base structure 235 that simulates the right rear third of the lower jaw. It includes apertures, sockets or openings 238, 239, 240 and 241 for teeth 250 to be used in training for treating tooth decay. The openings 238, 240 and 241 are designed to receive a single tooth 250 each. The opening 239 is wider than the others and receives multiple teeth 250, so that the teeth 250 therein can be set to simulate a close positioning.

A tongue 255 extends outwardly from the insert 204 and is shaped and sized to be received in one of the slots 230. Each of the openings 238, 239, 240 and 241 extend vertically part way through the insert 204. Glue or adhesive may be utilized to hold the tooth and a surrounding matrix 250 in the opening 238. A bore 261 extends through the base 235 and allows the alternative use of screw to hold the tooth 250 in the socket or opening 238. In use each of the openings 238, 239, 240 and 241 receive at least one tooth 250 for performing repair of dental decay procedures as described before. The insert 204 has an inward facing lip 257 near the bottom thereof for securing in place. A front 260 of the insert 204 has a recess 261 therein. Teeth 250 are placed in each of the openings 238, 239, 240 and 241 in the matrix 262 that gives slightly with pressure so as to simulate the ligaments that are attached to live teeth. Preferably, the matrix 262 is at least partly constructed of rubber, silicon or the like to provide some degree of flexure. It is foreseen that the top of the matrix 262 can be solid with the tooth 250 and only the bottom of a flexible material.

Figure 11:
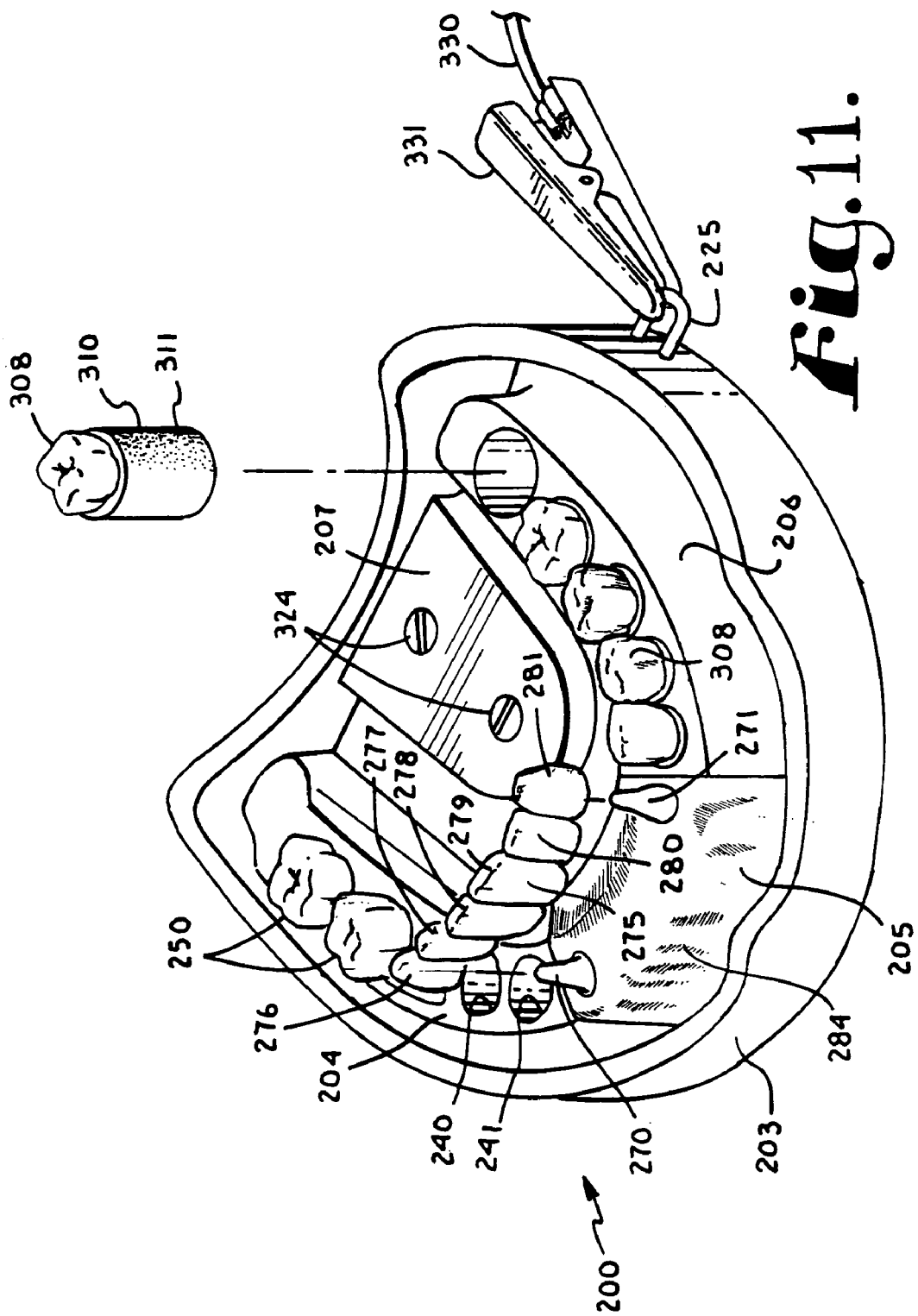
FIG. 11 is a perspective view of the third modified training aid showing the assemblage being prepared for and during specific dental training procedures.

The insert 205 is designed for crown and bridge work and in the present embodiment simulates the portion of the jaw normally holding the front 6 lower teeth of the mouth with the intent to use the two outer teeth for supporting a bridge. In particular, openings 266 and 267 are provided which receive and hold artificial or real teeth which are then ground by the student to provide supporting pegs 270 and 271, as shown in FIG. 11. The student prepares a bridge 275 with artificial teeth 276, 277, 278, 279, 280 and 281 that then set on and are adhered to the pegs 270 and 271 in a conventional manner. A drape 284 of polyurethane, silicon, rubber or the like extends over the insert 205 and simulates the flexibility and structure of gum tissue, since it is important for the student to carefully interact with gum in crown procedures.

The insert 205 also includes an outward facing tongue 290 that is positioned to fit in one of the slots 230 and an inwardly facing lip 291. On opposite ends of the insert 205 are position outward extending pegs 293 that are sized and shaped to be received in respective recesses in inserts 204 and 206 such as recess 261 in insert 204.

The insert 206 simulates the left side of the lower rear third of the jaw and includes six openings 300, 301, 302, 303 and 304 which are each sized to receive a tooth 308 and do extend to the bottom 307 of the insert 206. Each of the openings 300, 301, 302, 303, 304 and 305 are sized and shaped to receive a unit such as unit 310 which includes a tooth 308 and a surrounding conductive media 311. The units 310 are glued or otherwise affixed in the openings 300, 301, 302, 303, 304 and 305. The teeth 308 are preferably real teeth having a root canal. The student performs root canal procedures on the teeth 308 in the manner described before. The top part of the media 311 does not need to be conductive, but the lower portion onto which the tooth 308 root canal opens must be conductive between the tooth 308 and the plate 220. The material of the media 311 engages the plate 220 so as to provide a conductive path between the bottom of each tooth root and the ring 225. The insert 206 has a tongue 318 and a lip 319 similar to like structure found on the insert 204.

The securing plate 207 is sized and shaped to be secured to the base 211 using screws 324 set in apertures 325 that are received in bores 216 in the support 203. The securing plate extends outwardly toward each insert 204, 205 and 206 so as to cover the lips 257, 291 and 319 and so as to secure the inserts 204, 205 and 206 in the support 203 when secured in place by the screws 324.

In use the various inserts are used in the manner shown in FIG. 11. An electrode 330 attached by an alligator clip 331 to the conductive ring 225 when root cannel procedures are performed in any of the inserts 204, 205 or 206. The inserts 204, 205 and 206 are changed out as needed for other procedures or when expended to start new procedures.

It is foreseen that each insert would have an inwardly directed extension plate that could be attached by a single thumb screw, by multiple screws or the like to the support 203 and could replace the plate 207. Also, it is foreseen that an electrode could be attached to the plate 220 in a different manner than is shown which could replace the conductive ring 225.

It is to be understood that while certain forms of the present invention have been illustrated and described herein, it is not to be limited to the specific forms or arrangement of parts described and shown.

What is claimed and desired to be secured by Letters Patent is as follows:

1. A training device for use in practicing the correct positioning of an electrical apical locator comprising:
   a) a support structure having a cavity;
   b) a tooth having a root canal and being located partially in said cavity so that a crown of said tooth is exposed and a root of said tooth is received in said support structure cavity during usage;
   c) a matrix securely holding said tooth in a fixed position in said support structure cavity; and wherein
   d) at least a portion of said matrix in the region of a tip of said root is an electrically conductive medium selected to impart an impedance that approximates an impedance associated with normal human tissue surrounding a root of a live tooth.

2. The device according to claim 1 wherein:
   a) said support structure is an open topped enclosure suitable for holding by a user during usage.

3. The device according to claim 1 wherein:
   a) said support structure is a manikin device simulating a human jaw with the tooth mounted in said jaw.

4. The device according to claim 3 wherein:
   a) said jaw is a first jaw and said manikin includes a second articulated jaw.

5. The device according to claim 3 wherein:
   a) said manikin is at least partially electrically conductive between said device and a location for attachment to an apical locator.

6. The device according to claim 1 wherein:
   a) all of said matrix is conductive medium.

7. The device according to claim 1 wherein:
   a) said conductive medium is a first highly conductive matrix component that is located only in the vicinity of said root and a remainder of said cavity is filled with a second matrix component that is less electrically conductive than said first component.

8. The device according to claim 1 in combination with:
   a) an apical locator having a probe for insertion into said tooth root canal and an electrode adapted to be placed in electrical connection with said electrically conductive medium.

9. A teaching device for training dental students to locate a root canal apex in a tooth with an apical position locator; said device comprising:
   a) a manikin having at least one jaw that simulates a human jaw;
   b) said jaw having at least one socket therein located whereat a human tooth would be located in a human jaw;
   c) a tooth operably positioned in said socket such that a crown of said tooth extends outward from said socket and a root of said tooth is located in said socket; and
   d) a matrix securing said tooth in said socket; at least a first component of said matrix surrounding an apex of said tooth root being sufficiently electrically conductive so as to simulate the electrical conductance in human tissue surrounding a live tooth.

10. The device according to claim 9 wherein:
    a) said jaw is a first jaw and said manikin has a second jaw articulated with said first jaw.

11. The device according to claim 9 wherein:
    a) said first component is located only in close proximity to an apex of the tooth root.

12. The device according to claim 9 wherein:
    a) said matrix is essentially entirely composed of said first component.

13. The device according to claim 9 wherein:
a) said first component of said matrix includes at least 5% water by weight.

14. The device according to claim 9 wherein:
a) said first component of said matrix includes conductive metallic salt selected from the salts consisting essentially of sodium salts, calcium salts and mixtures thereof.

15. The device according to claim 9 wherein:
a) said first component of said matrix has a volume resistivity in the range from $10^{15}$ to $10^{-3}$ ohm/cm.

16. The device according to claim 9 including:
a) an apical position locator probe operably connectable to an apical locator device; said probe having a metallic central core with an exposed tip and having a shank covered by a non-conducting material.

17. A teaching device for training dental students to locate a root canal apex in a tooth with an apical position locator; said device comprising:
a) a manikin having at least one jaw that simulates a human jaw;
b) said jaw having at least one tooth that has said jaw molded thereabout and being located whereat a human tooth would be located in a live human jaw;
c) said tooth being operably positioned such that a crown of said tooth extends outward from said jaw and a root of said tooth is located in said jaw; and
d) a matrix having a first component surrounding an apex of said tooth root and being sufficiently electrically conductive so as to simulate the electrical conductance in human tissue surrounding a live tooth; said matrix first component being adapted to be operably conductively connected to such an apical position locator.

18. A training device for use in practicing the correct positioning of an electrical apical locator comprising:
a) a support structure having a cavity;
b) said support structure is a manikin device simulating a human jaw with the tooth mounted in said jaw;
c) said cavity is a socket sized and positioned in said manikin at a location whereat a tooth would be located in a human jaw;
d) a tooth having a root canal and being located partially in said cavity so that a crown of said tooth is exposed and a root of said tooth is received in said support structure cavity during usage;
e) a matrix securely holding said tooth in a fixed position in said support structure cavity;
f) a sleeve operably snugly received in said socket; said tooth and said matrix being located within said sleeve; and
g) at least a portion of said matrix in the region of a tip of said root is an electrically conductive medium selected to impart an impedance that approximates an impedance associated with normal human tissue surrounding a root of a live tooth.

19. The device according to claim 18 further including:
a) a pin operably extending between the manikin socket and sleeve so as to secure said sleeve in said socket.

20. The device according to claim 19 wherein:
a) said pin is a thumb screw having a head adapted to receive a connector of an apical position locator electrode; said head being exposed during use and an opposite end of said screw being sized and shaped to engage said conductive medium.

21. A training device for use in practicing the correct positioning of an electrical apical locator comprising:
a) a support structure having a cavity;
b) a tooth having a root canal and being located partially in said cavity so that a crown of said tooth is exposed and a root of said tooth is received in said support structure cavity during usage;
c) a matrix securely holding said tooth in a fixed position in said support structure cavity;
d) at least a portion of said matrix in the region of a tip of said root is an electrically conductive medium selected to impart an impedance that approximates an impedance associated with normal human tissue surrounding a root of a live tooth;
e) said conductive medium is a first highly conductive matrix component that is located only in the vicinity of said root and a remainder of said cavity is filled with a second matrix component that is less electrically conductive than said first component; and
f) a root sleeve sized and shaped to surround said first component and a tooth root apex, so as to hold said first component in position.

22. A teaching device for training dental students to locate a root canal apex in a tooth with an apical position locator; said device comprising:
a) a manikin having at least one jaw that simulates a human jaw;
b) said jaw having at least one socket therein located whereat a human tooth would be located in a human jaw;
c) a tooth operably positioned in said socket such that a crown of said tooth extends outward from said socket and a root of said tooth is located in said socket;
d) a matrix securing said tooth in said socket; at least a first component of said matrix surrounding an apex of said tooth root being sufficiently electrically conductive so as to simulate the electrical conductance in human tissue surrounding a live tooth; and
e) a matrix sleeve adapted to be snugly received in said socket and to receive said matrix and tooth within.

23. The device according to claim 22 including:
a) a pin to operably secure said matrix sleeve in said socket.

24. The device according to claim 23 wherein:
a) said pin is sized and positioned to have a tip end thereof engage said matrix first component and an opposite end adapted to be operably connected to a lead of an apical position locator.

25. A teaching device for training dental students to locate a root canal apex in a tooth with an apical position locator; said device comprising:
a) a manikin having at least one jaw that simulates a human jaw;
b) said jaw having at least one socket therein located whereat a human tooth would be located in a human jaw;
c) a tooth operably positioned in said socket such that a crown of said tooth extends outward from said socket and a root of said tooth is located in said socket;
d) a matrix securing said tooth in said socket; at least a first component of said matrix surrounding an apex of said tooth root being sufficiently electrically conductive so as to simulate the electrical conductance in human tissue surrounding a live tooth;
e) said first component is located only in close proximity to an apex of the tooth root; and
f) a tooth root sleeve sized and shaped to surround and protect said matrix first component and said tooth root apex during usage.

26. A dental teaching aid comprising:
a) a support structure having a generally planar support plate;
b) a plurality of inserts wherein each insert fits modularly on said support plate support structure and in abutting relationship to adjacent inserts;
c) each insert mimics a portion of a human jaw;
d) each insert provides structure thereon that allows a dental student to practice at least one dental procedure;
e) one of said inserts provides training structures for conducting root canals; and
f) said support includes an electrical conductor that is adapted to electrically contact said root canal insert so as to conduct electricity between a lower end of a root of a tooth and said conductor.

27. The training aid according to claim 26 wherein:
a) said electrical conductor comprises a metal plate positioned to operably engage all of said inserts.

28. A dental teaching aid comprising:
a) a support structure having a generally planar support plate;
b) a plurality of inserts wherein each insert fits modularly on said support plate support structure and in abutting relationship to adjacent inserts;
c) each insert mimics a portion of a human jaw;
d) each insert provides structure thereon that allows a dental student to practice at least one dental procedure;
e) one of said inserts provides training structures for conducting root canals;
f) each of said inserts includes an inward facing lip; and including
g) a plate that operably overlaps each insert lip and is securable to said support so as to lock said inserts to said support.

\* \* \* \* \*